Figure 1:
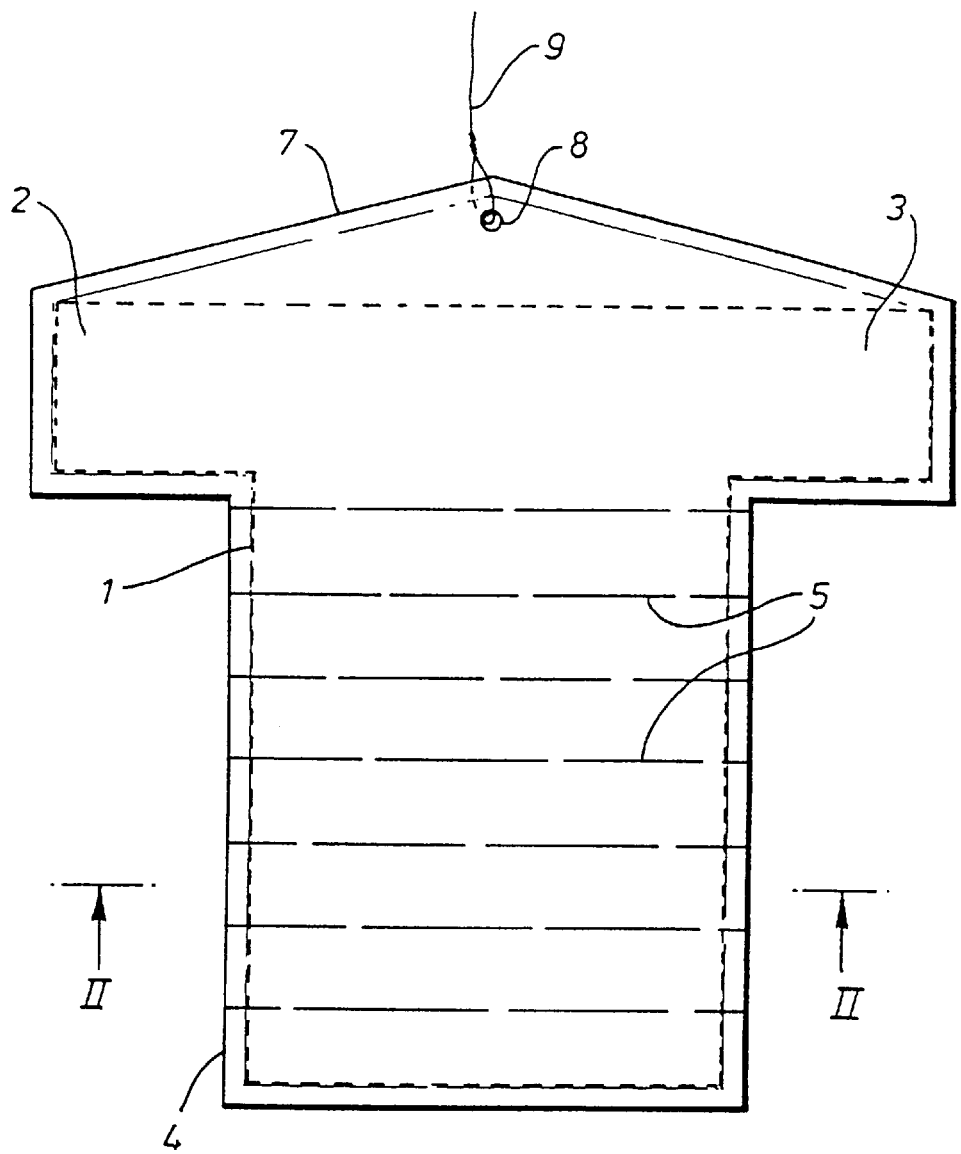

United States Patent [19]
Barlow et al.

[11] Patent Number: 6,012,643
[45] Date of Patent: Jan. 11, 2000

[54] DISPENSING DEVICE

[75] Inventors: Ian John Barlow, Wokingham; Keith J. Greatbatch, Finchampstead, both of United Kingdom

[73] Assignee: S.C. Johnson & Son, Inc., Racine, Wis.

[21] Appl. No.: 09/077,721

[22] PCT Filed: Dec. 5, 1996

[86] PCT No.: PCT/US96/19386

§ 371 Date: Oct. 5, 1998

§ 102(e) Date: Oct. 5, 1998

[87] PCT Pub. No.: WO97/20581

PCT Pub. Date: Jun. 12, 1999

[30] Foreign Application Priority Data

Dec. 5, 1995 [GB] United Kingdom .................... 9524804
Jun. 12, 1996 [GB] United Kingdom .................... 9612223

[51] Int. Cl.$^7$ ....................................................... A61L 9/04
[52] U.S. Cl. .................................. 239/6; 239/56; 239/58; 206/0.5; 206/466
[58] Field of Search ..................................... 239/6, 53–58, 239/60; 206/0.5, 466, 469

[56] References Cited

U.S. PATENT DOCUMENTS

| | | |
|---|---|---|
| 1,265,957 | 5/1918 | Ressler ....................................... 239/60 |
| 2,111,025 | 3/1938 | Galler ..................................... 239/57 X |
| 2,979,268 | 4/1961 | Brun ........................................ 239/60 X |
| 4,158,440 | 6/1979 | Sullivan et al. ........................... 239/56 |
| 4,712,737 | 12/1987 | Hecking .................................... 239/58 |
| 4,804,142 | 2/1989 | Riley ........................................ 239/56 |
| 4,960,240 | 10/1990 | McElfresh .............................. 239/57 X |
| 5,163,616 | 11/1992 | Bernarducci et al. ................. 239/60 X |
| 5,782,409 | 7/1998 | Paul ....................................... 239/58 X |

FOREIGN PATENT DOCUMENTS 68554 11/1944 Denmark ................................. 239/60

*Primary Examiner*—Andres Kashnikow
*Assistant Examiner*—Steven J. Ganey

[57] ABSTRACT

A device for the controlled release of vapour and a method of dispensing a volatile medium into the air. The device includes a carrier impregnated with a volatile medium and a wrapper of flexible material surrounding said carrier for retaining the volatile medium on the carrier. Said wrapper has a plurality of contiguous tear strips arranged in longitudinal sequence disposed over the carrier that may be successively removed to expose a portion of the carrier of increasing size without any need to provide for relative movement of the wrapper and carrier. The method of dispensing a volatile medium into the air includes providing such a device, removing a first tear strip to expose a portion of the carrier, and subsequently removing an additional tear strip to expose a fresh area of carrier to maintain the concentration of volatile medium at a desired level.

14 Claims, 2 Drawing Sheets

DISPENSING DEVICE

TECHNICAL FIELD

The present invention relates to a device for the controlled release of vapour.

BACKGROUND ART

There is a need for an improved simple dispensing device for dispensing vapour, for example, perfume, which gives a relatively uniform release of vapour over a prolonged period of time.

DISCLOSURE OF INVENTION

According to the present invention, a device for the controlled release of vapour comprises:

a) a carrier impregnated with a volatile medium;
b) a wrapper of flexible material surrounding said carrier for retaining the volatile medium on the carrier, said wrapper having a plurality of tear strips disposed over the carrier.

In one preferred aspect of the present invention, the tear strips are contiguous so that it is possible by removing successive tear strips to expose a single, increasing, area of the carrier.

In another preferred aspect of the invention the tear strips extend over at least 50% of the whole area of the carrier, more preferably over at least 60% of the whole area. Most preferably, the tear strips may extend over at least 80% of the whole area of the carrier.

In a further preferred aspect of the present invention, at least two tear strips are arranged in longitudinal sequence over the carrier. Thus, all the tear strips may be arranged in longitudinal sequence over the carrier.

The carrier is conveniently a flat sheet, e.g., a card formed from wood pulp. The thickness of the sheet is preferably in the range 1 to 4 mm. Thick sheets give greater mechanical strength to the device. Thin, more dense sheets reduce the tendency of volatile medium to diffuse through the carrier and escape from the exposed surfaces of the carrier.

The volatile medium may be a medium which releases a perfume (or fragrance) when exposed to the air. Suitable volatile media are well-known for use in air fresheners. The volatile medium may be applied to the carrier by any convenient method, e.g., by impregnation with liquid.

The wrapper of flexible material may be any material which will control the volatile medium escaping into the atmosphere around the device and which can be provided with tear strips. The wrapper may, for example, be formed of a synthetic polymer film, for example, a polyethylene film, e.g., low density polyethylene (LDPE) or ethylene vinyl alcohol copolymer (EVOH). The thickness of the film may be, for example, in the range of 20 micrometres to 500 micrometres.

With the device of the present invention, there is no need to provide either for relative movement of the wrapper and carrier or for diffusion of vapour from areas of the carrier which cannot be exposed by removing a tear strip. It is therefore possible, and desirable, to make the wrapper a tight fit on the carrier, subject to manufacturing constraints. Preferably, the wrapper is a sufficiently tight fit on the carrier that significant quantities of volatile medium, e.g., perfume, do not escape through any space between the carrier and the wrapper. Such quantities shall be deemed "significant" if their escape interferes with the effective or convenient stepped release of volatiles by successive removal of tear strips, as is described below. Thus, in the case of a sheet carrier, the space between an edge of the sheet and the corresponding edge of the wrapper is preferably less than 10 mm, more preferably less than 5 mm.

The wrapper is provided with tear strips. Tear strips are portions of the wrapper which can be manually detached from the remainder of the wrapper without the need for a tool, e.g., scissors. Tear strips are produced by providing preformed lines of weakness in the wrapper. In principle, tear strips can be provided by providing lines of perforation. However, unless the perforated area is small, volatile medium will tend to escape through the perforations so reducing the shelf life, i.e., the period after manufacture for which the device retains it useful properties. It is therefore preferred to produce the tear strips by providing lines of weaknesses which do not extend fully through the thickness of the material forming the wrapper. Such lines of weakness may be produced by the technique of laser etching. Wrapping films with lines of weakness produced by laser etching may be obtained from L.P.F. Laser Systems of Leeuwarden, The Netherlands.

The tear strips are preferably constructed so that they are completely removable from the wrapper. Preferably, where a flat carrier is used, removal of a tear strip exposes both sides of the carrier.

As indicated above, the tear strips are preferably contiguous.

Again, as indicated above, the area provided with tear strips can extend over substantially the whole area of the carrier. Preferably, at least 50%, more preferably, at least 60%, for example, at least 80%, e.g., at least 90% of the area of the card can be exposed by the removal of tear strips.

The tear strips are preferably disposed such that at least two are in longitudinal sequence over the carrier. In other words, a straight line over the surface of the carrier passes through each tear strip in the longitudinal sequence in turn. The tear strips may be disposed along the longest dimension of the carrier. This will facilitate the provision of a relatively large number of tear strips. However, the tear strips may be disposed in sequence along a shorter dimension of the carrier and the dimensions of the tear strips adjusted accordingly.

By providing tear strips in longitudinal sequence, a large number of zones can be provided to give controlled release over an extended period of time.

Preferably, at least four tear strips are provided, e.g., at least 5 tear strips may be provided.

The device will generally be used with the carrier in a vertical position so as to expose the maximum surface area for the release of volatile medium when the tear strips are removed. Preferably, the device is provided with suspending means so that it can be freely suspended in an air space, e.g. within a vehicle. The suspending means may, for example, be a cord or hook attached to the wrapper.

It is preferred to provide retaining means for retaining the carrier within the wrapper when it is suspended vertically rather than relying merely on the tightness of fit of the wrapper. The retaining means may be a portion of the carrier with a wider dimension than the remaining parts which cooperates with a corresponding part of the wrapper. It is preferred to have a carrier in the form of a flat sheet having a broadest portion at its upper end at less than 50% of the length of the sheet from the top of the sheet, more preferably, less than 40%. By having the broadest dimension at the upper end of the carrier, it is easier to arrange for a greater area of the carrier to be exposed by the removal of tear strips while allowing the remaining part of the wrapper to support the carrier. When referring to top and bottom in relation to the carrier, reference is made to its suspended position when in use, and references to length are to the vertical direction when freely suspended and breadth are to the horizontal direction when freely suspended.

Alternatively, a plastic moulding with a channel may grip the carrier and the wrapper to hold them together and may be provided with a suspending means. The device of the present invention is particularly useful for use as a deodorant in the drive and/or passenger compartments of motor vehicles. By removing a first tear strip, deodorizing perfume is released into the atmosphere in the motor vehicle from the carrier. When the available perfume has been released from a first area of exposed carrier, a second tear strip can be removed to expose a fresh area of carrier to maintain the concentration of perfume at a desired level.

The present invention includes the use of the vapour dispensing device of the invention to maintain a level of vapour in an enclosed space by the successive removal of tear strips as the concentration of vapour falls.

BEST METHOD OF CARRYING OUT THE INVENTION

Figure 2:
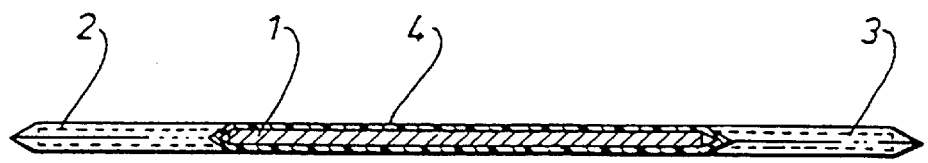
Figure 3:
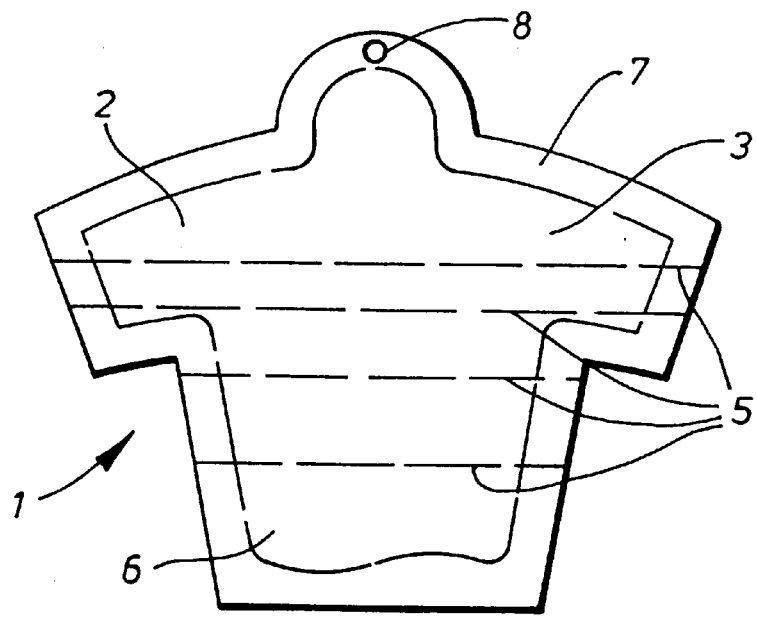
Figure 4:
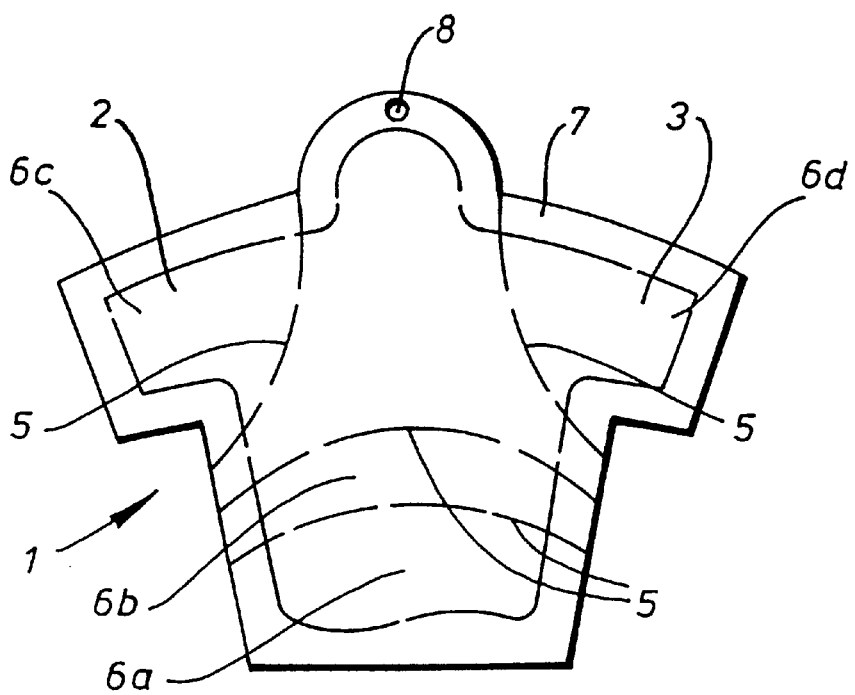

The invention will now be described with reference to the accompanying diagrammatic drawings in which:

FIG. 1 is a plan view of a device according to the present invention, suitable for use as a deodorizing device in a motor vehicle, FIG. 2 is a cross-section (not to scale) taken along the line II—II of FIG. 1, FIG. 3 is a plan view of an alternative form of a device according to the invention, and FIG. 4 is a plan view of a further alternative form of the invention.

The device comprises a carrier (1) in the form of a flat, T-shaped card of vegetable fibre, e.g., wood pulp, impregnated with perfume by conventional methods. The card has a main rectangular portion of length of about 8 mm. and a width of about 60 mm. At one end of this main portion there are two rectangular projections (2,3) extending for about 25 mm from the main body of the card(1). The card is covered with a closely fitting wrapping (4) (or envelope) of flexible material, namely, low density polyethylene film of a type conventionally used in packaging and having a thickness of 60 micrometres.

The clearance between each edge of the card and the corresponding edge of the wrapper is of the order of 3 mm.

A plurality of lines of weakness (5) is provided in the film. These lines extend laterally across the card to divide the film into a plurality of contiguous tear strips arranged in longitudinal sequence along the card. Each tear strip can be removed manually in sequence starting from the narrow end of the card. The lines of weakness are provided by the known technique of laser etching.

A portion (7) of the film extends beyond the broadest part of the card and is provided with a perforation (8) through which a length of string (9) may be passed to provide a suspending means to enable the device to be suspended. The two opposed sides of the wrapper are fused or heat-sealed together in the vicinity of the perforation (8) to prevent the escape of perfume from the card.

When the card is suspended vertically, e.g., within the passenger space of a motor vehicle, successive areas of the card can be exposed by removing successive portions of the wrapper, starting at the bottom. The projecting portions (2, 3) act as retaining means to prevent the card from falling out of the wrapper.

Referring now to FIG. 3, the carrier (1) is in the form of a flat card as in FIG. 1. The card has a curved upper portion extending to form two arms (2, 3). The maximum distance across the arms is about 103 mm. The greatest distance from top to bottom of the card is about 87 mm. The card is covered with a wrapping of envelope of flexible material (4) as in FIG. 1. The wrapping is formed by sealing two sheets, placed over and under the card, at their overlapping edges around the card. The seal between the two sheets is indicated at (7). The seal extends to within a short distance of the card so that the film wrapper is a tight fit on the card.

A plurality of lines of weaknesses (5) is provided in the film, dividing the film into four contiguous tear strips (6) arranged in longitudinal sequence starting from the bottom end of the card. The tear strips extend around the card so that removal of a tear strip exposes both sides of the card. The dimensions of the tear strips are selected so that the area of the card exposed by the removal of each tear strip is substantially the same, although the shapes of the tear strips are all different. The surface area of card exposed when all the tear strips are removed is about 66% of the total surface area of the card. The portion of the plastics film which is not removed as a tear strip extends over the widest portion of the card, which thus retains the plastics film on the card, even when all the tear strips are removed.

The dispenser is provided with a suspending means in the form of a perforation (8) extending through a portion of the seal (7) extending around the card. Plastic fasteners for inserting in the perforation (8) to facilitate the attachment of perforated articles to hooks are well-known. Alternatively, a length of string may be inserted into the perforation.

FIG. 4 shows a device using a card and plastics film of the same overall shape as FIG. 3. However, the arrangement of tear strips is different. There are two contiguous tear strips (6a, 6b) in longitudinal sequence along the carrier. These are of different shapes but are approximately the same area. There are two further non-contiguous tear strips with the same shape (6c, 6d) which are of lower surface area than the first mentioned tear strips and which extend over the arms (2,3). The portion of the plastics film which remains after all the tear strips have been removed extends around a portion of the card which is narrower than the portion of the card above it, so helping to retain the film wrapper on the card.

We claim:

1. A device for the controlled release of vapour comprising:
   a. a carrier impregnated with a volatile medium;
   b. a wrapper of flexible material surrounding said carrier for retaining the volatile medium on the carrier, said wrapper having a plurality of contiguous tear strips arranged in longitudinal sequence over the carrier that may be successively removed to expose a portion of the carrier of increasing size without any need to provide for relative movement of the wrapper and carrier.

2. A device according to claim 1, wherein there are at least four contiguous tear strips.

3. A device according to any of the preceding claims wherein the tear strips, taken together, extend over at least 50% of the area of the carrier.

4. A device according to claim 3, wherein the tear strips extend over at least 60% of the area of the carrier.

5. A device according to claim 1, wherein the carrier is a flat sheet.

6. A device according to claim 5 wherein the sheet has its broadest portion at its upper end at less than 50% of the length of the carrier from the top of the sheet.

7. A device according to claim 6, wherein the broadest portion is at less than 40% from the top of the sheet.

8. A device according to claim 1, wherein the carrier is a card of wood pulp.

9. A device according to claim 1, wherein the wrapper is a tight fit on the carrier to retard the escape of volatile medium through any space between the carrier and the wrapper.

10. A device according to claim 1, wherein the wrapper is a synthetic polymer film.

11. A device according to claim 1, having at least 5 tear strips.

12. A device according to claim 1, wherein the tear strips are constituted by lines of weakness produced by laser etching.

13. A device according to claim 1, having suspending means for suspending the device in an air space.

14. A method of dispensing a volatile medium into the air comprising the steps of
  a. providing a device for the controlled release of vapour in accord with claim 1;
  b. removing a first tear strip to expose a portion of the carrier; and
  c. subsequently removing successive additional tear strips to expose fresh areas of carrier to maintain the concentration of volatile medium at a desired level.

* * * * *